United States Patent [19]

Lekholm

[11] Patent Number: 4,760,852
[45] Date of Patent: Aug. 2, 1988

[54] HEART PACEMAKER ELECTRODE HAVING TWO PORTIONS OF DIFFERENT CONDUCTIVE PROPERTIES FOR STIMULATING AND SENSING

[75] Inventor: Anders Lekholm, Bromma, Sweden

[73] Assignee: Siemens Aktiengesellschaft, Berlin and Munich, Fed. Rep. of Germany

[21] Appl. No.: 904,101

[22] Filed: Sep. 4, 1986

[30] Foreign Application Priority Data

Sep. 9, 1985 [DE] Fed. Rep. of Germany ....... 3532084

[51] Int. Cl.$^4$ ............................................. A61N 1/04
[52] U.S. Cl. .................................... 128/785; 128/783; 128/784; 128/786
[58] Field of Search ......................... 128/783, 784, 785

[56] References Cited

U.S. PATENT DOCUMENTS

| 3,911,928 | 10/1975 | Lagergren | 128/419 P |
| 3,964,469 | 6/1976 | Manley | 128/641 |
| 3,977,411 | 8/1976 | Hughes, Jr. et al. | 128/419 P |
| 4,011,861 | 3/1977 | Enger | 128/642 |
| 4,407,302 | 10/1983 | Hirshorn et al. | 128/784 |
| 4,534,366 | 8/1985 | Soukup | 128/419 P |
| 4,603,704 | 8/1986 | Mund et al. | 128/784 |
| 4,630,611 | 12/1986 | King | 128/419 P |
| 4,643,193 | 2/1987 | DeMarzo | 128/640 |

FOREIGN PATENT DOCUMENTS

| 0032356 | 12/1980 | European Pat. Off. |
| 0142079 | 6/1981 | European Pat. Off. |
| 2952818 | 7/1981 | Fed. Rep. of Germany ...... 128/785 |

OTHER PUBLICATIONS

Siemens Brochure "Endocardial Leads 411S, 412S, 412M, 422S, 422M".

Primary Examiner—William E. Kamm
Assistant Examiner—Timothy Keegan
Attorney, Agent, or Firm—Hill, Van Santen, Steadman & Simpson

[57] ABSTRACT

A heart pacemaker electrode for stimulating and detecting heart voltages, has an electrode head at the distal, heart-proximate end, which functions to both stimulate the heart by supplying pulses thereto, and to sense heart activity. The surface of the electrode head is divided into portions which, although electrically connected, exhibit different impedances. Once portion has a lower impedance, which primarily functions for stimulating the heart, and the other portion has a higher impedance which functions in combination with the portion of lower impedance during sensing. The electrode head thus in totality exhibits a low impedance for stimulating the heart, permitting a high current density to be achieved, while exhibiting an overall high impedance for sensing.

4 Claims, 1 Drawing Sheet

HEART PACEMAKER ELECTRODE HAVING TWO PORTIONS OF DIFFERENT CONDUCTIVE PROPERTIES FOR STIMULATING AND SENSING

BACKGROUND OF THE INVENTION

1. Field of the Invention

The present invention relates to a heart pacemaker electrode of the type permanently attached to the heart for stimulating the heart by means of pulses supplied by the pacemaker, and for sensing heart activity.

2. Description of the Prior Art

Heart pacemaker electrodes are known which include at least one electrical conductor surrounded by an insulating sheath, which is inert to body fluid. The lead is provided with a conductive electrode head at its distal end, i.e., the heart-proximate end. Such heart pacemaker electrodes can be employed both for stimulating the myocardium and for detecting heart voltages. In order to maintain the necessary stimulation energy as low as possible, the current density should be as high as possible. This is achieved in the simplest manner by making the surface of the electrode head as small as is reasonably possible. When such electrodes are employed for sensing QRS potentials, they have a relatively high source impedance on the order of magnitude of 10-20 kohms, given a smooth electrode head surface. Because the input impedance of the pacemaker amplifiers generally lies on the same order of magnitude, these heart signals are greatly attenuated in the input stage. The sensing characteristics can be improved in the simplest manner by enlarging the conductive surface of the electrode head. The demands on the size of the electrode surface for simulating and sensing are thus competing, which has required conventional pacemaker electrodes to undertake an optimization as to electrode head surface area.

The problem of competing demands on the size of the electrode head surface, however, can also be resolved in other ways, for example, by making the surface of the electrode head micro-porous. As a result, current is concentrated during stimulation and thus the desired high current density is obtained, whereas the boundary surface from electrode head to electrolyte is large enough to obtain a low source impedance when sensing heart signals. Such electrode heads are known, for example, from a Siemens brochure describing endocardial electrodes having an electrode head of glassy carbon, dated March 1984 (A. 91003-M3372-L745-02-4J00).

A heart pacemaker electrode for simultaneous stimulation or sensing is also known from EP-A No. 0 032 356 or from U.S. Pat. No. 3,977,411. In this pacemaker electrode, two separate surfaces of respectively different sizes are separated from each other by an insulating layer. A larger of the surfaces functions as a sensing surface and is connected to the common conductor via a relatively high impedance resistor, and thus that surface does not substantially contribute to the current output during stimulation. The conductivity of the stimulation and sensing surfaces is the same, relative to the surface area.

SUMMARY OF THE INVENTION

It is an object of the present invention to provide a heart pacemaker electrode which exhibits good stimulation and sensing properties, and allows freedom in the three-dimensional design of the electrode head.

Another object of the present invention is to provide such an electrode head which is simple to manufacture.

The above objects are achieved in accordance with the principles of the present invention in an electrode head which has two surfaces for stimulation and sensing of the heart which have respectively different impedances. The impedance of the sensing surface is selected such that the current concentrates primarily on the stimulation surface during stimulation, however, both surfaces are effective during sensing. In contrast to known heart pacemaker electrodes, for example, the aforementioned electrode described in U.S. Pat. No. 3,977,411, no galvanic separation between the surfaces is necessary, and an additional resistor between one of the surfaces and the electrode conductor is not needed.

The two surfaces of differing impedance can be formed in the simplest way by materials having different conductivity. Thus, for example, the electrode head may have a relatively small-area tip exhibiting good conductivity (low impedance) functioning as the stimulation surface. This tip occupies the extreme distal portion of the electrode. A larger surface is disposed adjacent the tip which has a lower conductivity (high impedance). During stimulation, therefor, the current will be concentrated at the extreme tip because the impedance to the surrounding tissue is relatively low, for example, 500-1000 ohms. During sensing, by contrast, the entire surface of the electrode head will be effective, because the source impedance of the electrode head can amount to several kohms without substantially influencing the sensing properties. In other words, the structure disclosed herein makes use of the perception that a large difference in impedance exists at the boundary between the electrode head surface and the surrounding electrolyte, this difference being dependent on whether low or high electrical signals are being conducted.

Instead of using different materials, the different impedances can alternatively be achieved by different surface treatments of the same material. Thus, for example, the higher impedance portion of the electrode head may have a smooth surface, while the lower impedance portion may have a microporous surface. In one embodiment of the electrode, the stimulation surface may consist of metal or a metal compound, and the sensing surface may consist of conductive plastic inert to body fluid. As described above, the tip of the electrode head can consist of material having lower impedance suitable for stimulation. It is also possible, however, to divide the surface having lower impedance, i.e., the stimulation surface, into a plurality of regions and to distribute these regions either uniformly or non-uniformly over the full surface of the electrode head, or over a portion of this surface. Thus, the regions of lower impedance can be annularly distributed around the electrode head. It is also possible to arrange the regions in the form of longitudinal strips or in a screen-like criss-crossing pattern. Due to the distribution of regions for stimulating the heart over the larger electrode head surface, the advantage is obtained that at least some of these distributed regions are sure to establish contact with body tissue exhibiting good conductivity, and thus the stimulation threshold can be maintained low.

Particularly in the embodiment wherein a conductive plastic is employed as the sensing surface, a further advantage is obtained in that this plastic can simultaneously function for fixing the electrode head in the heart trabeculae, this surface being selectively shaped for this purpose. Retaining elements can be formed from the plastic in the shape of bristles or fins, or as a collar, and can occupy a relatively large surface which greatly increases the sensing sensitivity. The retaining elements can be provided for passive or active fixing of the electrode.

It is also possible that the retaining elements can consist of the material having higher impedance, and thus the retaining elements function to stimulate the heart.

DESCRIPTION OF THE PREFERRED EMBODIMENTS

Figure 1:
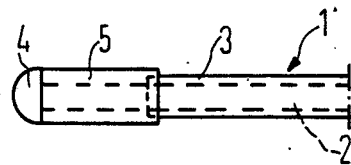
FIG. 1 is a side view of an electrode head of a pacemaker electrode constructed in accordance with the principles of the present invention.

FIG. 1 shows a first embodiment of an electrode head for a heart pacemaker lead constructed in accordance with the principles of the present invention, the lead or cable being generally referenced at 1. In FIG. 1, as in the other figures, the illustration is schematic and not necessarily true-to-scale.

In FIG. 1, an electrical conductor 2 extends internally within the lead 1, and is surrounded by an insulating sheath 3. The conductor 2, at its distal end, is connected to a tip 4. The surface of the tip 4 may be smooth or micro-porous, and the tip 4 may consist of metal, a metal compound, or carbon. The tip 4 has a low impedance (high conductivity) and is well suited for stimulating heart tissue. The surface of the tip 4 is made as small as possible in order to achieve a sufficiently high current density and may, for example, have a surface area of approximately ten square millimeters. Proceeding in a direction away from the extreme distal end, the tip 4 is followed by a ring or cylinder 5 which is electrically connected to the tip 4. The ring 5 may consist, for example, of a conductive elastomer or of a metal exhibiting low conductivity (high impedance). The ring 5 may alternatively consist of a metal compound or a ceramic compound. The surface area of the ring 5 is larger than that of the tip 4. As a result of the lower conductivity of the ring 5, substantially no current is conducted through this surface during stimulation. The conductivity of the ring 5, however, is high enough such that, when sensing heart voltages, these signals are picked up by the ring 5 in combination with the tip 4.

Figure 2:
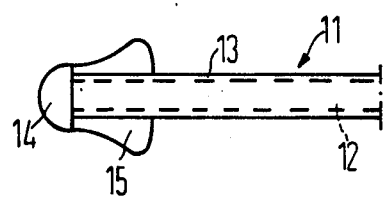
FIG. 2 is a side view of a further embodiment of an electrode head constructed in accordance with the principles of the present invention.
Figure 3:
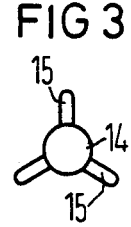
FIG. 3 is an end view of the electrode shown in FIG. 2.

A further embodiment of an electrode head in accordance with the principles of the present invention is shown in two views in FIGS. 2 and 3. In this embodiment, the lead or cable is generally referenced 11, and again includes an internal conductor 12 and an insulating sheath 13. The embodiment of FIGS. 2 and 3 has a plurality, such as three, fin-like projections 15 electrically connected to a tip 14. The projections 15 are formed of a material having lower conductivity than the tip 14. The projections 15 may consist of a conductive elastomer. In addition to serving the purpose of enlarging the surface of the elctrode head effective for sensing heart voltages, the projections 15 simultaneously function for passively fixing the electrode head to the heart tissue.

Figure 4:
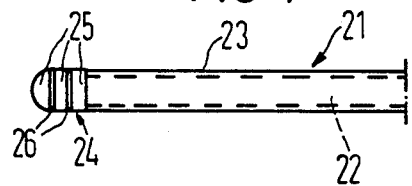
FIG. 4 is a side view of another embodiment of an electrode head constructed in accordance with the principles of the present invention.

Another embodiment is shown in FIG. 4 wherein the lead is generally referenced at 21 and includes an internal electrical conductor 22 and an insulating sheath 23. In this embodiment, an electrode head is generally referenced at 24. The surface of this electrode head primarily consists of regions 25 having lower conductivity. Two regions 26 which may, for example, be annular surfaces, are provided between the surfaces 25. The surfaces 26 have a higher conductivity and function for stimulating heart tissue.

Figure 5:
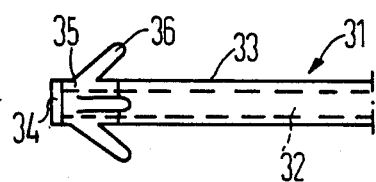
FIG. 5 is a side view of a still further embodiment of an electrode head constructed in accordance with the principles of the present invention.
Figure 6:
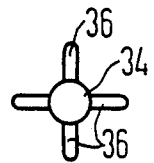
FIG. 6 is an end view of the electrode head shown in FIG. 5.

Another embodiment is shown in FIGS. 5 and 6 wherein the lead or cable is generally referenced at 31 and includes an internal electrical conductor 32 and an insulating sheath 33. The embodiment of FIGS. 5 and 6 has a flat tip 34 consisting of material having a low impedance at the extreme distal end. The tip 34 is followed by a ring 35 consisting of a conductive elastomer from which bristle-like projections 36 extend. The projections 36 may be slanted away from the tip 34 and function as passive retaining elements. These elements may consist of the same material as the ring 35.

Although modifications and changes may be suggested by those skilled in the art, it is the intention of the inventor to embody within the patent warranted hereon all changes and modifications as reasonably and properly come within the scope of his contribution to the art.

I claim as my invention:

1. An electrode head for a distal, heart-proximate end of a heart pacemaker lead comprising:

a high conductivity tip portion of said electrode head and a low conductivity tail portion of said electrode head, said high and low conductivity portions being disposed adjacent to each other and being electrically connected, said high conductivity tip portion comprising a tip area of said electrode head that is substantially smaller in area than said low conductivity tail portion, said low conductivity portion including conductive flexible plastic projections that extend rearwardly from said tip area adapted for engaging heart trabeculae to retain said tip and tail portions in electrical contact with heart tissue, said high conductivity portion having a conductivity selected for applying stimulation pulses to said heart primarily only via said high conductivity tip portion, and said low conductivity tail portion having a conductivity selected such that both high conductivity and low conductivity portions of said electrode head are effective for sensing signals from said heart, said low conductivity tail portion being effective for sensing signals from a larger area within said heart than is said high conductivity tip portion.

2. An electrode head as claimed in claim 1, wherein said stimulation portion has a micro-porous surface.

3. An electrode head as claimed in claim 1, wherein said stimulation portion consists of metal.

4. An electrode head as claimed in claim 1, wherein said stimulation portion consists of a metal compound.

* * * * *